United States Patent [19]

Wodlinger et al.

[11] Patent Number: 4,521,186
[45] Date of Patent: Jun. 4, 1985

[54] SYSTEM FOR DETERMINING THE FIRST PREMATURITY CONTACT OF DENTAL OCCLUSION

[76] Inventors: Harold Wodlinger, 614 Yorkhill Blvd., Thornhill, Ontario, Canada, L4J 3J7; Hart V. Katz, 23 Wyvern Rd., Willowdale, Ontario, Canada, M2K 2K3

[21] Appl. No.: 495,555

[22] Filed: May 17, 1983

[51] Int. Cl.³ ............................................. A61C 9/00
[52] U.S. Cl. ....................................... 433/71; 128/777
[58] Field of Search ................... 433/71, 68; 128/642, 128/774, 776, 777, 782

[56] References Cited

U.S. PATENT DOCUMENTS

| | | | |
|---|---|---|---|
| 3,349,489 | 10/1967 | Shackelford | 433/68 |
| 3,883,954 | 5/1975 | Simmering et al. | 433/68 |
| 3,983,865 | 10/1976 | Shepard | 128/777 |
| 4,232,687 | 11/1980 | Shanklin | 128/777 |
| 4,287,895 | 9/1981 | Hori | 128/777 |
| 4,334,542 | 6/1982 | Takinishi et al. | 128/787 |
| 4,386,405 | 5/1983 | Lewin et al. | 128/777 |
| 4,402,326 | 9/1983 | Okano et al. | 433/68 |

FOREIGN PATENT DOCUMENTS

| | | | |
|---|---|---|---|
| 0066173 | 12/1982 | European Pat. Off. | 128/777 |
| 465196 | 6/1975 | U.S.S.R. | 433/68 |

OTHER PUBLICATIONS

"Dynamic Palatometry", Fletcher et al., Jo. of Speech and Hearing Res., 12-1975, pp. 812-818.
"Video-Scanning System for Measurement of Lip and Jaw Motion", McCutcheon et al., J. Acoust. Soc. Am., vol. 61, No. 4, 4-1977, pp. 1051-1055.

*Primary Examiner*—John J. Wilson
*Attorney, Agent, or Firm*—McCarthy & McCarthy

[57] ABSTRACT

A system for determining the first dental occlusion prematurity is presented. A sensor adapted to be inserted in the mouth of a patient comprises two flexible strips with spaced electrical conductors connected to a liquid crystal display. Each of the strips has a layer of dilatant material on one side. When the patient bites, the upper and lower conductors complete an electrical circuit and from the resistance of this circuit the location of the first prematurity relative to the strip is determined. One edge of the strip is used as a reference point on the sensor and the distance from this edge to the location is displayed on the liquid crystal display. The dilatant layer also retains the impression of the teeth and the location identified by the visual display and the impression are compared to give the exact location of the first prematurity. The sensor is reusable on the same patient to determine subsequent prematurities by squeezing it to remove the impression of teeth on the original bite.

9 Claims, 8 Drawing Figures

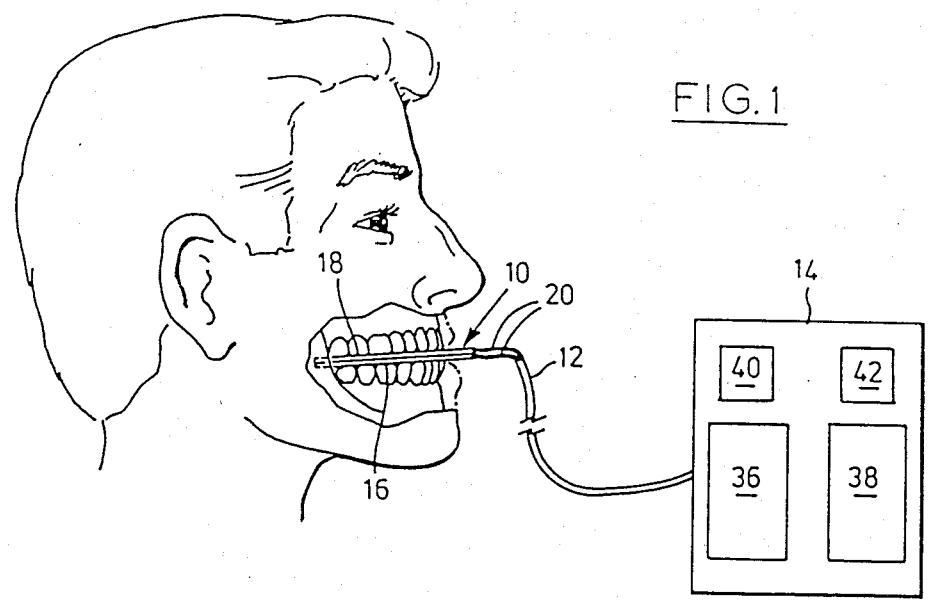
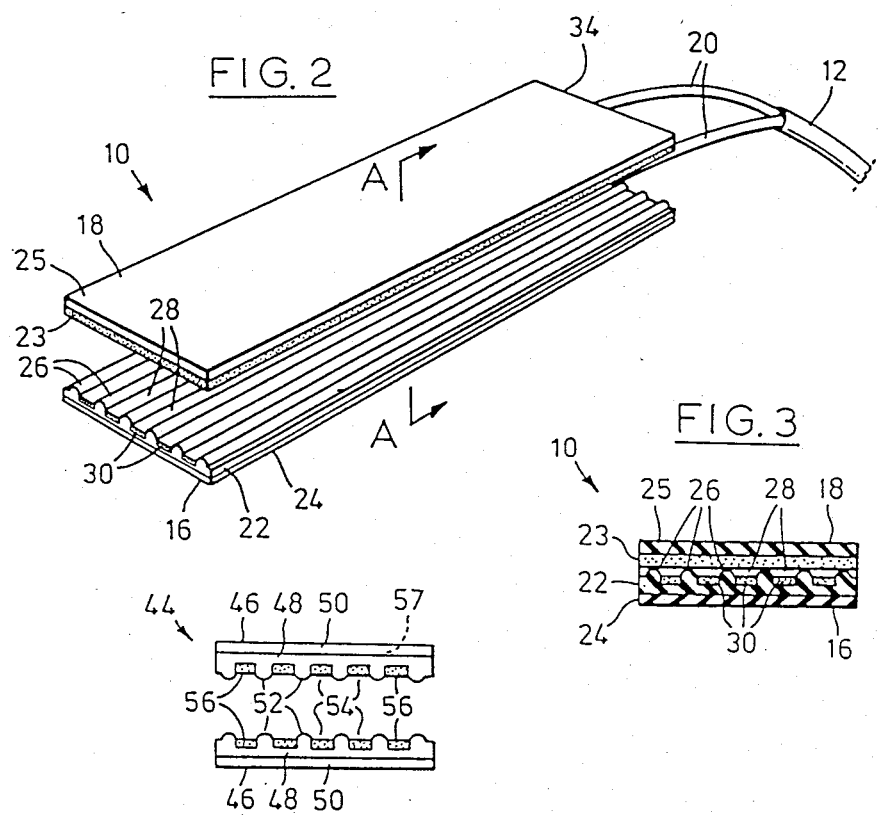

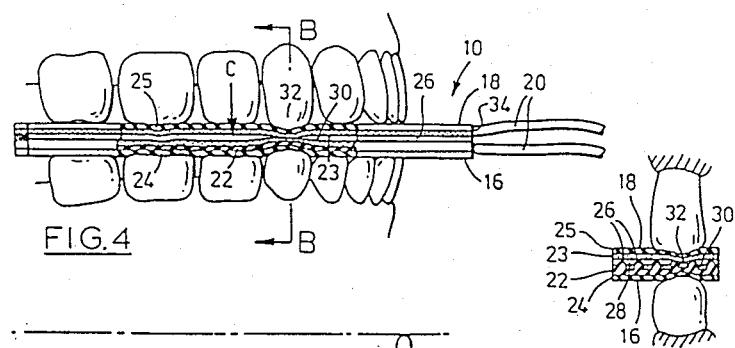
FIG. 4
FIG. 5
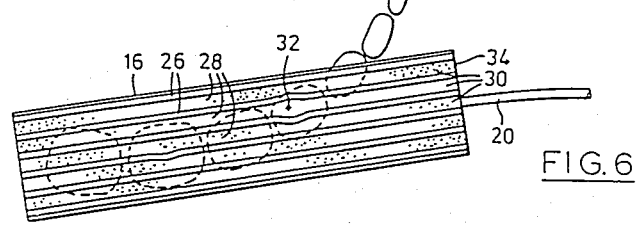
FIG. 6
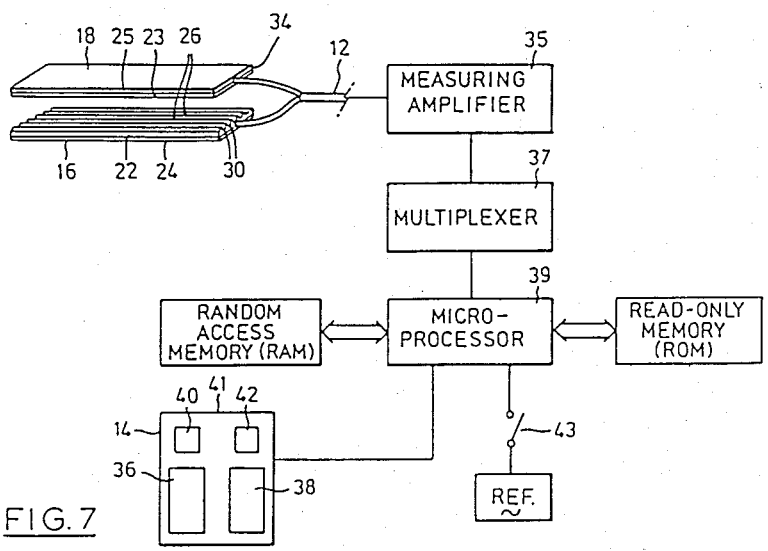
FIG. 7

SYSTEM FOR DETERMINING THE FIRST PREMATURITY CONTACT OF DENTAL OCCLUSION

The present invention relates to a system for determining the first prematurity contact of dental occlusion. In particular, the invention also relates to a dental occlusion sensor and to apparatus for processing the information provided by the dental occlusion sensor.

In order for the dental clinician to provide quick and accurate occlusion adjustment, not only the set of premature contacts requires to be known but also the location of the first premature contact needs to be determined since this first contact predominantly influences dental occlusion. A reliable, rapid and accurate system for automatically providing such information would not only improve the dentist's efficiency during equilibration but would also ensure that increased benefit was obtained to the patient.

U.S. Pat. No. 3,349,489 to Shackleford discloses a pressure sensitive dental device for measuring relative occlusion pressure. This prior patent shows a device adapted to be positioned between the teeth of a patient, and has inner and/or outer flanges which engage the lingual and/or buccal sides of sets of natural or artificial teeth to aid in placing and holding the device in desired position between the teeth during a test bite. This prior device also has two electronic wafer-shaped pressure sensitive cells in insulated compartments or areas between each pair of occluding teeth; one cell responding to and measuring pressures exerted between the mating lingual cusps, and the other cell between tne mating buccal cusps of each pair of posterior teeth. For the anterior six pairs of teeth the pairs of cells are very closely spaced so as to indicate whether or not there is a true occlusion therebetween.

In this prior device, all of the cells have a common or ground conductor which is a flat horseshoe shaped sheet of metal foil or a laminar conductor coated or printed on the device; or a similarly shaped added or inserted element. Each cell has a live lead wire, which lies within or along margins of the device and is led away from an end of the device in a single cable containing the ground conductor and 32 signal conductors, one from each cell. During a bite test all cells can be read simultaneously from meters and the dentists then use this information to grind the teeth to give the optimum pressure pattern.

One significant disadvantage of this apparatus is the complexity of the sensor and associated signal processing circuitry which increases manufacturing costs. Another disadvantage is that the meters used have a relatively long response time and consequently it is very difficult to find the location of the first occlusal prematurity with any degree of accuracy. This device also gives an indication of contact in terms of pressure but the highest pressure does not necessarily indicate the point at which the first occlusal prematurity occurs. to interpret the results in such a way could result in serious consequences.

In addition, although there is a sensor for the lingual and buccal compartments of each pair of teeth the cells of the sensor are too large to discriminate between prematurities on the same tooth, and this can lead to an ambiguous result and incorrect dental treatment. Also, the set up time for each measurement is too long because of identification of each tooth.

It is an object of the present invention to obviate or to mitigate the aforesaid disadvantages.

In one aspect of the present invention there is provided a system with a sensor insertable between the teeth which, as the patient bites, electrically measures the distance of the first prematurity from a reference point using an electrical resistance technique, and presents this information in a visible manner to give a clear and unambiguous result, the distance measured by electrical resistance being correlated with a dental occlusion impression taken simultaneously using impressionable means during the bite to determine the tirst occlusion prematurity.

In the preferred embodiment, the sensor comprises first and second planar strips of the same dimensions, one strip having a plurality of parallel elongate conducting elements spaced apart by parallel elongate insulating elements. The insulating elements are thicker than the conducting elements to give a ribbed arrangement. The other strip is planar and of substantially the same dimensions and is conducting. Each strip has an impressionable means in the form of a dilatant material layered with it, the dilatant material being deformable to retain an impression on the teeth. Dilatant materials have mechanical properties such that their stiffness and resistance to shear increases as more shear is applied to the material. When the material is subjected to pressure, it responds by flowing and deformating and when the pressure is released, the material will gradually return to its original shape, e.g. under its own weight. Dilatant materials are well known and described and documented in the literature. Many uncured silicone rubbers exhibit dilatant properties, and these constitute the dilatant materials used in the sensor. They may be compounded to a stiff, semi-solid, putty-like consistency, e.g. by mixing with compatible fillers, such as precipitated silica. Alternative compatible fillers for such rubbers are well known in the art, and are useful in the present invention, in a range of 0–100 parts by weight, per one hundred parts by weight of uncured silicone rubber. Siloxane rubber, such as dialkylsiloxane are suitable.

The most preferred class of materials for use in the present invention are uncured methylvinylsiloxane rubber polymers, of the low molecular weight range (molecular weights about 10,000–100,000), the silicon atoms in the chain structures of which have been partially replaced by boron atoms, from the addition of boric acid during the polymerisation of the polymer, to give a boron:silicon atomic ratio in the final product of 1:3 to about 1:100. Boronated methylvinylsiloxane rubbers may be compounded, with up to an equal weight of conventional, compatible filler such as precipitated silica.

Examples of such partially boronated methylvinylsiloxane rubbers exhibiting satisfactory dilatant properties are readily available commercially on the market. One such material is marketed under the trade mark "Silly Putty", as a children's toy.

The conducting elements are connected by a lead to a signal processing and control unit which has a visual display, preferably a liquid crystal display. The control unit scans the conductors continuously, and the signal processing circuitry determines the electrical resistance between the conductive elements and the conductive strip. Normally the electrical resistance is infinite as there is no physical contact. In use, the strips are located opposite each other between the teeth and on biting, the first dental prematurity contact causes contact at a point between a particular conducting element on the first strip and the second strip.

The control unit of the signal processing circuitry which scans the conductors of each strip recognizes when there is electrical contact between conductors of opposite strips due to a reduction in electrical resistance measured. The electrical resistance of the current path is measured and this value is directly related, by calibration, to the length of the conductors in the circuit and thus the distance from a reference point to the prematurity occlusion is calculated. Thus knowing the location of the reference point gives the location of the first prematurity on the sensor. The distance is visually displayed on a liquid crystal display screen and the co-ordinates of the location are also displayed. This location may then be identified on the impression left on the dilatant material so that the dentist can then accurately locate the first prematurity from the impression, and hence accurately modify the dental occlusion.

Embodiments of the present invention will now be described by way of illustrative example with reference to the accompanying drawings in which:

FIG. 1 is a schematic view showing a sensor inserted on a mouth between upper and lower teeth and connected to signal processing display means;

FIG. 2 is a prespective view of the sensor strip;

FIG. 3 is a cross-section view taken on the line A—A of FIG. 2 with the sensor in an assembled condition;

FIG. 4 is a detailed cut-away side view of a sensor when the sensor is located between the teeth during a bite;

FIG. 5 is similar to FIG. 3 and is a cross-sectional view through FIG. 4 on B—B;

FIG. 6 is a view taken in the direction of arrow C of FIG. 4;

FIG. 7 is a schematic block diagram of the signal processing and display circuit, and FIG. 8 which appears on the same sheet as FIG. 1 is an end view of an alternative sensor to that shown in FIG. 3.

Referring now to FIG. 1 of the drawings, a sensor, generally indicated by reference numeral 10, is located in the mouth of a patient between upper and lower teeth. The sensor is connected by a connector 12 to a signal processing and display unit 14. The sensor has two flexible strips 16 and 18 each of which is ½ inch wide by 2 inches long connected to the connector 12 by leads 20. As shown in FIG. 2 strip 16, is rectangular and is a laminate of a silicone rubber insulating material 22, and boronated methylvinylsiloxane dilatant material 24 known as SILLY PUTTY TM. Strip 18 is the same size and shape and is a laminate of a conductive layer 23 and a boronated methylvinylsiloxane dilatant layer 25 known as SILLY PUTTY TM. The conducting layer 23 is made of carbon-impregnated silicone rubber.

The silicone rubber 22 of strip 16 has parallel longitudinal ribs 26 integral with and upstanding from the plane of the strip. Adjacent upstanding ribs define five longitudinal channels or grooves 28 in which five conductors 30 are located. The conductors 30 are silicon rubber impregnated with graphite particles and are integral with the insulating material 22. The conductors 30 have a known value of electrical resistance per unit length for their cross-sectional shape. In use the two strips 16 and 18 of sensor 10 are located opposite each other as shown in FIGS. 1 and 3. The ribs 26 and the channels or grooves 28 thus lie opposite the conducting surface 23 and in the absence of deformation the ribs 26 keep the conductors of the same strip, and, of the opposite strip separated. When the sensor is inserted and the patient bites as shown in FIGS. 4 and 5, the sensor is initially deformed as the upper and lower teeth close at the location of the first occlusion prematurity and this causes the conductive layer 23 of the upper strip 18 to contact a conductor 30 in the lower strip 16 at point 32. The contact point 32 completes an electrical circuit, part of which is the resistance of the conductor 30 in the lower strip and the resistance of the conducting strip between the end 34 and the contact point 32. The resistance of the conducting strip 23 is very small in comparison to the resistance of the conductor 30 or part thereof and its effect on the overall measurement of resistance is negligible.

As shown in FIG. 7 the signal processing and display unit 14 is connected to the sensor conductors by connector 12. For clarity the signal processing circuitry is shown external to the unit 14. Conducting leads (not shown) are connected from each of the conductors 23, 30 via connector 12 to the measuring amplifier 35. A multiplexor 37 under the control of a microprocesser 39 continually scans the resistance of the branch of the circuit containing the conductors 23 and 30 for each conductor 30. Normally, as there is no contact between the conductors 23, and 30 the circuit is open and the resistance is infinite. Upon biting, the conductors 23 and a conductor 30 are brought into contact by a first dental occlusion prematurity, as at point 32, and the multiplexor 37 scanning the sensor detects a signal corresponding a finite value of resistance is detected. This detected signal is amplified by a measuring amplifier 35. Sequential scanning of the conducting ships permits identification in the lateral direction of the conducting strips. The particular conductor completing the electrical circuit is recognized by the control unit. The value of the resistance initially detected determines the distance from the edge 34 of the conductor 32, which serves as a reference point. As shown in FIG. 7 the output of the sensor is connected to a measuring amplifier 35 which is connected to a multiplexor 37, tne output of which is connected to the microprocessor 39. The microprocessor 39 has a read-only-memory (ROM) containing the programs for operation of the system under the control of the microprocesssor 39, for storing the resistances measured at first prematurity occlusion and a random-access-memory (RAM). The microprocessor decodes the information of the resistance change and transmits it to a display unit 41 in accordance with a predetermined algorithm and the ROM. The display unit 14 has liquid crystal displays with LCD screens 36 and 38 for left and right sensors respectively, each of screens 36, 38 has smaller screens 40, 42 associated with it. The microprocessor also has an input which enables the system to be calibrated via a switch 43 and reference input signals. In this example as the first prematurity is on the right side of the mouth the location of the prematurity is displayed on liquid crystal display screen 38. This may be achieved using a switch on the unit selectable by the dentist. The numerical co-ordinates of the prematurity locations are displayed on the smaller liquid crystal display screen 40. The co-ordinates indicate the lateral location of the prematurity in the plane of the sensor: in the example shown, the prematurity is at the second conductor from the right and 5 distance units from the reference point 34 (FIG. 6). Calibration and knowledge of the dimensions of the sensor and its components permit the prematurity location on the sensor to be identified. The impression of the teeth on the dilatant layer enables correlation of this location with the teeth in the patient so that the tooth at which premature occlusion occurs can be identified, thus the exact location of the first occlusal prematurity can be determined. The deformation or impression can be easily erased by the dentist by pulling the strip between his finger and thumb whilst squeezing it to enable it to be re-used on the same patient.

In another embodiment of the invention as shown in FIG. 8, in the sensor 44 both of the strips 46 are identical to strip 16, that is an electrically insulating layer 48 laminated with an impressionable layer 50. Each strip 46 has ribs 52 defining channels or grooves 54 in which conductors 56 are formed by carbon impregnation. This operates in a similar manner to the sensor of the preferred embodiment but is somewhat more difficult to use and the contact between opposite conductors has been found to be less effective than the contact of the preferred embodiment, though still satisfactory. However, this arrangement is just as accurate with regard to giving distance of the first prematurity from the reference point 57. Correlation with the deformations in the deformable layer yields information about the occlusion prematurity which is just as accurate as with the preferred embodiment.

Without departing from the scope of the invention it should be understood that various modifications can be made to the embodiments described. For example, the number of conductors in one strip can be varied, five conductors gives sufficient resolution across the width of the tooth to overcome most ambiguities concerning first prematurity location, however even three conductors or more gives satisfactory results; the dilatant material may be replaced by other material which deforms to retain an impression of the teeth during a bite although it should also be recognised that it should be compatible for use in the clinical field. The conductors and the insulating strips should also be mechanically and biologically compatible and other suitable materials may be any flexible biocompatible polymer and flexible conducting material. In this regard doping the polymer with metal particles to give conductive region is within the ambit of the invention. The display could be of any type equivalent to a liquid crystal display such as electroluminsent, light emitting diode, etc. Although the preferred embodiment specifies a size suitable for adult mouths, it will be appreciated that a scaled down version may be made for children. Also two sensors could be used simultaneously with the first occlusion prematurity being indicated on either the left or the right side of the display according to whether the occlusion prematurity, is on the left or the right side of the mouth. Advantages of the embodiments as described are that the sensors are reusable for a particular patient, and that they are also disposable after use. The system is such that the location of the first occlusion prematurity is fast, the impression permitting immediate identification, and accurate, and the process can be rapidly and accurately repeated on the same patient with the same sensor to determine subsequent first occlusion prematurities until the dentist has obtained satisfactory dental occlusion adjustment.

What we claim is:

1. A sensor for determining the first dental occlusion prematurity comprising first and second planar portions, said first planar portion having a layer of an insulating material with a plurality of elongate parallel ribs extending longitudinally of said portion, adjacent pairs of ribs defining channels therebetween, conducting elements located in these channels, the second portion having a layer of a planar conducting material, the first and the second portions also having a dilatant layer of boronated methylvinylsiloxane polymer on one side thereof and having substantially the same shape thereas, said polymer being deformable from one position to another position and retaining its deformation thereat whereby in use the first and the second portions are adapted to be inserted in the mouth of a patient such that the first and second portions are located opposite each other; the ribs separating the conducting elements in the first planar portion from the conducting layer of the second planar portion.

2. A sensor as claimed in claim 1 wherein in response to a bite the sensor is deformed such that the dilatant material retains an impression of the teeth and a conductive element of the first planar portion and the second conducting portion are forced into contact, said contact defining a contact path which completes an electrical current path.

3. A sensor as claimed in claim 1 wherein the insulating material is silicone rubber, the conductors being carbon-impregnated silicon rubber which are integral with the insulating material, and the layer of conducting material is carbon-impregnated silicone rubber.

4. A sensor for determining the first dental occlusion prematurity comprising first and second planar portions, each of said first and said second planar portions having a layer of insulating material with a plurality of parallel elongate ribs extending longitudinally of said portion, adjacent pairs of ribs defining channels therebetween, conducting elements located in these channels, each planar portion having a dilatant layer on one side thereof, said dilatant layer being boronated methylvinylsiloxane polymer, said polymer being deformable from one position to another position and retaining its deformation thereat, the dilatant layer being substantially of the same shape as the first and second portions, whereby in use said first and said second portions are adapted to be located in the mouth of a patient such that the ribs and the conductive portions of one portion are located opposite respective ribs and conductive portions of the other portion.

5. A sensor as claimed in claim 4 wherein in response to a bite the sensor is deformed such that the dilatant material retains an impression of the teeth and a conductive element of the first planar portion is forced into contact with a conductive element of the second planar portion, said contact defining a contact point which completes an electrical current path.

6. A sensor as claimed in claim 4 wherein the insulating material is silicone rubber the conductors being carbon-impregnated silicone rubber.

7. A method of determining the first dental occlusion prematurity comprising:
inserting a sensor into the mouth of a patient between the upper and lower teeth, the sensor having an upper and a lower portion; each portion having conductive elements, the conducting elements of respective upper and lower portions being normally non-contacting;
causing the patient to close his mouth to bite the sensor between his upper and lower teeth so that the upper and lower conductors come into contact;

measuring an electrical parameter between the upper and the lower conductors when in contact;

processing the electrical parameter measurement in accordance with calibration values to provide the location of the first dental occlusion prematurity with respect to a reference point on the sensor;

displaying the location of the first dental occlusion prematurity on display means;

recording the impression of the teeth simultaneously at occlusion using a dilatant layer connected to the sensor;

correlating the location on the display with the location of the first prematurity from the impressionable material.

8. A method as claimed in claim 7 including erasing the impression of the teeth on the dilatant layer and reusing the sensor to determine subsequent first prematurities on the same patient.

9. A method as claimed in claim 7 wherein the electrical resistance between the upper and lower conductors is measured when said upper and lower conductors are in contact.

* * * * *